United States Patent [19]
Wolpe et al.

[11] Patent Number: 5,700,466
[45] Date of Patent: Dec. 23, 1997

[54] METHOD OF AMELIORATING OR PREVENTING SEPTIC SHOCK USING A MONOCLONAL ANTIBODY SPECIFIC TO CACHECTIN/TUMOR NECROSIS FACTOR

[75] Inventors: Stephen D. Wolpe, Arlington, Mass.; Anthony Cerami, Shelter Island, N.Y.

[73] Assignee: The Rockefeller University, New York, N.Y.

[21] Appl. No.: 348,764

[22] Filed: Dec. 2, 1994

Related U.S. Application Data

[63] Continuation of Ser. No. 286,477, Dec. 19, 1988, abandoned, which is a continuation-in-part of Ser. No. 766,852, Aug. 16, 1985, abandoned, which is a continuation-in-part of Ser. No. 414,098, Sep. 7, 1982, Pat. No. 4,603,106, which is a continuation-in-part of Ser. No. 351,290, Feb. 22, 1982, abandoned, which is a continuation-in-part of Ser. No. 299,932, Sep. 8, 1981, abandoned.

[51] Int. Cl.$^6$ .................... A61K 39/395; A61K 39/40; A61K 38/19; C07K 16/24
[52] U.S. Cl. .................... 424/145.1; 424/130.1; 424/141.1; 424/150.1; 424/158.1; 530/387.1; 530/388.1; 530/388.2; 530/388.23; 530/388.4
[58] Field of Search .................... 424/150.1, 164.1, 424/145.1, 141.1, 158.1, 130.1; 530/388.1, 388.23, 388.4, 387.1, 388.2

[56] References Cited

U.S. PATENT DOCUMENTS 5,231,024  7/1993  Moeller et al. .................... 435/240.27

OTHER PUBLICATIONS

Abraham, E. et al., Jama, 273(12):934–941, Mar. 1995.
Natanson, C. et al., Annals of Int. Med., 120(9):771–783, 1 May 1994.
Cross, A.S. et al., Inf. & Immun., 61(7):2741–2747, Jul. 1993.
Makato Hirai et al., Production & characterization of monoclonal anti-bodies to human tumor necrosis factor, JOURNAL OF IMMUNOLOGICAL METHODS, 96 (1987), 57–62.
Chi-Ming Liang et al., Production & characterization of monoclonal anti–bodies against recombinant human tumor necrosis factor/cachectin, BIOCHEMICAL & BIOPHYSICAL RESEARCH COMMUNICATION, vol. 137, No. 2 (1986).
Daniela N. Mannel et al., Inhibition of nonspecific tumoricidal activity by activated macrophages with antiserum against a soluble cytotoxic factor, INFECTION AND IMMUNITY (Jul., 1981), 156–164.
Bong–Sop Shim et al., The nature of endotoxin–induced tumor necrosis factor, BIOLOGICAL ABSTRACTS, vol. 69, No. 2 (Jan. 15, 1980).
Tracey, et al., 1986, "Shock and Tissue Injury Induced by . . . " Science 234: 470–474.
Bentler, et al., 1985 "Passive Immunization Against Cachectin 1 tumor necrosis factor . . . " Science 229: 869–871.
Bringman et al., 1987 "Monoclonal antibodies to human tumor necrosis factors . . . " Hybridoma 6(5): 489–507.
Mc Namara, et al., 1984, "Monoclonal Idiotope Vaccine . . . " Science 220: 1325–1326.
Fink, et al. 1990, "Laboratory models of Sepsis . . . " J. Surgical Res 49: 186–196.
Verhoef, et al, 1990, "Prospects for monoclonal antibodies . . . " Eur. J. Clin. Microbiol. Infect. Dis. 9(4): 247–250.
Fitzer–Schiller, 1993 "Centocor Stops trials of Flagship Drug" Wash. Post Jan. 18, 1993.
Stone, 1993, "Biotec Industry Reels on Sepsis".

*Primary Examiner*—Susan A. Loring
*Attorney, Agent, or Firm*—Klauber & Jackson

[57] ABSTRACT

The present invention pertains to the novel hybridoma SDW18.1.1, hybridomas obtained from SDW18.1.1, monoclonal antibodies obtained from such hybridomas and derivatives of such monoclonal antibodies. The novel hybridomas are formed by fusion of cells from a mouse myeloma line and spleen cells from a mouse previously immunized with cachectin/TNF. Diagnostic and therapeutic utilities for the monoclonal antibodies and their derivatives are proposed, and testing procedures, materials in kit form and pharmaceutical compositions are likewise set forth.

2 Claims, No Drawings

METHOD OF AMELIORATING OR PREVENTING SEPTIC SHOCK USING A MONOCLONAL ANTIBODY SPECIFIC TO CACHECTIN/TUMOR NECROSIS FACTOR

RELATED APPLICATIONS

The present application is a continuation of application Ser. No. 07/286,477, filed Dec. 19, 1988, now abandoned, which is a continuation-in-part of application Ser. No. 766,852, filed Aug. 16, 1985 now abandoned, which is a continuation-in-part of Ser. No. 414,098, filed Sep. 7, 1982, now U.S. Pat. No. 4,603,106, issued Jul. 29, 1986, which is in turn a continuation-in-part of Ser. No. 351,290, filed Feb. 22, 1982, now abandoned, which is in turn a continuation-in-part of Ser. No. 299,932, filed Sep. 8, 1981, also abandoned, in all of which at least one of the Applicants herein is a co-inventor. Applicants claim the benefit of these applications under 35 U.S.C. Section 120.

RELATED PUBLICATIONS

The Applicants are authors or co-authors of several articles directed to the subject matter of the present invention. These articles are in supplementation to those articles listed in U.S. Pat. No. 4,603,106, which earlier articles are incorporated herein by reference. (1) [Applicant Cerami co-authored with B. Beutler, J. Mahoney, N. Le Trang and P. Pekala] "Purification of Cachectin, a Lipoprotein Lipase-Suppressing Hormone Secreted By Endotoxin-Induced RAW 264 7 Cells", J. EXP. MED. 161 at 984–995 (May, 1985); (2) [Applicant Cerami co-authored with J. R. Mahoney, B. Beutler, N. Le Trang, W. Vine, and Y. Ikeda] "Lipopolysaccharide-Treated RAW 264.7 Cells produce a Mediator Which Inhibits Lipoprotein Lipase in 3T3-L1 Cells", J. IMMUNOL. 134 (3) at 1673–1675 (March, 1985); (3) [Applicant Cerami co-authored with P. J. Hotez, N. Le Trang, and A. H. Fairlamb] "Lipoprotein Lipase Suppression in 3T3-L1 Cells by a Haematoprotozoan-Induced Mediator From Peritoneal Exudate Cells", PARASITE IMMUNOL. (Oxf.) 6:203 (1984); (4) [Applicant Cerami co-authored with B. Beutler, D. Greenwald, J. D. Hulmes, M. Chang Y.-C. E. Pan, J. Mathison and R. Ulevitch] "Identity of Tumor Necrosis Factor and Macrophage-Secreted Factor Cachectin", NATURE 316:552–554, (1985); (5) [Applicant Cerami co-authored with B. Beutler, F. M. Torti, B. Dieckmann and G. M. Ringold] "A Macrophage Factor Inhibits Adipocyte Gene Expression: An In Vitro Model of Cachexia", SCIENCE 229:867–869, (1985); (6) [Applicant Cerami co-authored with B. Beutler and I. W. Milsark] "Passive Immunization Against Cachectin/Tumor Necrosis Factor (TNF) Protects Mice From the Lethal Effect of Endotoxin", SCIENCE 229:869–871, (1985); (7) [Applicants Cerami and Wolpe co-authored with K. J. Tracey, B. Beutler, S. F. Lowry, J. Merryweather, I. W. Milsark, R. J. Hariri, T. J. Fahey III, A. Zentella, J. D. Albert and G. T. Shires] "Shock And Tissue Injury Induced By Recombinant Human Cachectin", SCIENCE 234:470–474 (1986); and (8) [Applicant Cerami co-authored with K. J. Tracey, Y. Fong, D. G. Hesse, K. R. Manogue, A. T. Lee, G. C. Kuo and S. F. Lowry] "Anti-Cachectin/TNF Monoclonal Antibodies prevent Septic Shock During Lethal Bacteraemia", NATURE 330:662–664 (Dec. 17, 1987). All of the above listed articles are incorporated herein by reference.

BACKGROUND OF THE INVENTION

The present invention is directed to new hybrid cell lines and more specifically to hybrid cell lines for production of monoclonal antibody to cachectin/TNF, to the antibody so produced, to antibodies raised thereto, and to diagnostic and therapeutic methods and compositions employing these antibodies.

The development of monoclonal antibodies has made possible new diagnostic and therapeutic techniques. Monoclonal antibodies are homogeneous immunoglobulins of well-defined chemical structure in contrast to polyclonal antibodies which are heterogeneous mixtures of immunoglobulins. A characteristic feature of monoclonal antibodies is high specificity and reproducibility of function.

The technique for producing monoclonal antibodies from hybridized cells (hybridomas) was first described by Kohler and Milstein [NATURE 256:495–497 (1975)]. The hybridomas are produced by fusion of mouse myeloma cells with spleen cells from immunized mice or rats. Clones of the hybridoma cells (cells arising from a single parent plasmacytoma spleen fusion cell) are then tested for their ability to produce the desired monoclonal antibody. Each clone produces only a single antibody type directed against a single antigen only and is therefore highly specific. In contrast to conventional (polyclonal) antibody preparations which typically include different types of antibodies directed against different sets of determinants (sites) on the same antigen, monoclonal antibody preparations are directed only against a single determinant.

Although the general procedures for preparing hybridomas are known, there is no certainty that the desired hybridoma will be obtained, that the hybridoma obtained will produce the desired antibody and that the antibody obtained will have the desired degree of specificity. The level of success is chiefly dependent upon the type of antigen employed during the immunization procedure and the selection technique employed for isolating the desired hybridoma.

One of the areas of interest for using monoclonal antibodies is in the diagnosis and treatment of biochemical derangements that occur in mammalian hosts responding to invasive stimuli. These gross imbalances of host physiology are generally manifested as a wasting of the body (cachexia) which itself may threaten the integrity of the host. These metabolic disorders seem to be mediated largely by the immune system. For example, in response to invasive stimuli, the reticuloendothelial cells and lymphocytes secrete cytokines which are capable of altering host metabolism. These cytokines include for example, Interleukin-1, Interleukin-2, lymphotoxin, gamma-interferon and the substance known as either cachectin or tumor necrosis factor (TNF).

Systemic deficiency of the anabolic enzyme lipoprotein lipase (LPL) activity has been observed in cachectic animals. Deficiency of LPL activity has also been observed in mice after administration of endotoxin (lipopolysaccharide, LpS). In contrast, deficiency of LPL activity has not been observed in mice genetically resistant to LPS. Resistance to endotoxin-induced LPL deficiency could be overcome by administration of serum obtained from endotoxin-sensitive animals which had been previously injected with LPL. The active factor in this serum was termed "cachectin" because of its involvement in the pathogenesis of cachexia [M. Kawakami et al., PROC. NATL. ACAD. SCI, (USA), 79:912–916 (1982)].

The existence of a factor which caused hemorrhagic necrosis of tumors, in the serum of endotoxin-treated animals previously infected with Mycobacterium bovis strain Bacillus Calmette-Guerin was also observed. The active principal in this serum was termed "tumor necrosis factor" [E. A. Carswell et al., PROC. NATL. SCI. (USA), 72:3666–3670 (1975)].

The potent tumor necrosis factor activity of cachectin in vitro and DNA sequencing of the primary structure of cachectin and tumor necrosis factor confirmed that these polypetides are homologous molecules and that their bioactivities are both derived from a highly conserved protein. Accordingly, the term "cachectin/TNF" will be used when referring to these factors herein.

Cachectin/TNF is a polypeptide hormone composed of subunits having a relative molecular mass of 17,000 arranged in dimeric, trimeric or pentameric form depending upon the species and the method of isolation. When administered to animals in moderate amounts, cachectin/TNF induces a state of anorexia and ensuing weight loss. Cachectin/TNF also seems to play a major role in the pathogenesis of Gram-negative (endotoxin-induced) shock. Not only does the administration of large doses of cachectin/TNF directly mimic the clinical syndrome produced by endotoxemia [K. J. Tracey et al., SCIENCE 234:470–474 (1986)], but passive immunization against cachectin/TNF substantially mitigates the lethal effect of endotoxin [K. J. Tracey et al., NATURE 330:662–664(1987)]. Cachectin/TNF has the ability to substantially suppress the activity of the anabolic enzyme LPL and is capable of preventing the differentiation of fat cells and increasing the uptake of glucose in muscle cells. Cachectin/TNF demonstrably lacks leukocyte activator activity which characteristic distinguishes it from Interleukin-1. Similarly, the ability of cachectin/TNF to significantly suppress LPL activity distinguishes it from Interleukin-2. These findings were set forth in copending parent application Ser. No. 766,852, the disclosure of which is incorporated herein by reference.

Most cell types express specific high-affinity cell-surface receptors for cachectin/TNF, but the consequences of binding the cytokine are diverse and often cell- and species-specific. Certain cell types show marked sensitivity to the cytotoxic effects of cachectin/TNF while others bind the cytokine but are not deleteriously affected. Other cell types respond to cachectin/TNF treatment with specific and well coordinated changes in the activity, expression, synthesis, or release of surface or cytosolic proteins, enzymes, or further physiological mediators. Much research over the past few years has focused on dissecting apart these differential biological effects of cachectin/TNF and an important step in this direction would be the identification and characterization of cachectin/TNF receptors from various cellular sources.

Accordingly, there exists a need for antibodies in relatively pure form for the detection and study of cachectin/TNF. More particularly, there exists a need for monoclonal antibodies to cachectin/TNF for use in the diagnosis and treatment of cachexia and related diseases.

SUMMARY OF THE INVENTION

The present invention pertains to the novel hybridoma SDW18.1.1, hybridomas obtained from SDW18.1.1, monoclonal antibodies obtained from such hybridomas, derivatives of such monoclonal antibodies and the use of such monoclonal antibodies and their derivatives of diagnostic and therapeutic methods and compositions. The novel hybridomas are formed by fusion of cells from a mouse myeloma line and spleen cells from a mouse previously immunized with cachectin/TNF.

Accordingly, it is a principal object of the present invention to prepare a monoclonal antibody to cachectin/TNF.

It is a further object of the present invention to employ the monoclonal antibody to detect and study as aforesaid the activity of cachectin/TNF.

It is a still further object of the present invention to employ the monoclonal antibody as aforesaid to diagnose and treat biological derangements in which cachectin/TNF is implicated.

It is a still further object of the present invention to prepare additional antibodies from the monoclonal antibody as aforesaid which may be used in further diagnostic and therapeutic settings because of their ability to bind to the cellular receptor for cachectin/TNF.

Other objects and advantges will become apparent to those skilled in the art from a consideration of the ensuing description.

DETAILED DESCRIPTION

The present invention concerns the preparation and use of a monoclonal antibody to cachectin/TNF. The particular monoclonal antibody prepared and discussed herein was raised against human tumor necrosis factor. It is understood however that the preparation and application of the antibody described herein extends to monoclonal antibodies based on other sources of cachectin/TNF and is therefore, intended to encompass such variations in source within its scope.

The novel monoclonal antibodies of the present invention provide a high titer, reproducible, biological reagent for the assay of cachectin/TNF. Fluids or tissues from a variety of mammals can be screened by radioimmunoassay, enzyme immunoassay, immunofluorescence, complement fixation, immunoprecipitation or any reaction which depends upon antibody recognition of antigen for the detection of cachectin/TNF. Furthermore, the novel monoclonal antibodies of the present invention are useful in the diagnosis and treatment of cachexia and related diseases.

The hybridoma SDW18.1.1 was deposited at the American Type Culture Collection, 12301 Parklawn Drive, Rockville, Md. 20852 for patent purposes as defined in M.P.E.P. 608.01(p) on Oct.15, 1986 and was given the A.T.C.C. Accession No. HB 9228.

In general, the method of preparing the hybridoma of the present invention comprises the following steps: (a) immunizing mice with cachectin/TNF; (b) removing the spleens from the mice and preparing an immunized spleen-cell suspension; (c) fusing the suspended spleen cells with mouse myeloma cells from a suitable cell line using a fusion promoter; (d) diluting and culturing in separate wells the mixture of unfused spleen cells, unfused myeloma cells, and fused hybrid cells in a selective medium which will not support the unfused myeloma cells for a time sufficient to allow the death of the unfused cells; (e) evaluating the supernatant in each well containing the hybridoma for the presence of antibodies to cachectin/TNF; and (f) selecting and cloning hybridomas producing the desired monoclonal antibodies.

The immunization schedule and the concentration of cachectin/TNF should be such that useful quantities of primed splenocytes are obtained. Freund's adjuvant may be used to prime the immune system. After centrifugation and washing, the immunized spleen cells are ready to be fused with mouse myeloma cells. Suitable fusion promoters are polyethylene glycol (PEG) and dimethyl sulfoxide (DMSO).

The myeloma cell lines chosen should preferably be the drug resistant type such as the 8-azaguanine resistant cell lines which lines are deficient in the enzyme hypoxanthine guanine ribosyl transferase (HPRT) or thymidine kinase. The lack of these specific enzymes in these lines makes it impossible for these myeloma cells to incorporate exogenously supplied hypoxanthine or thymidine. Endogenous DNA synthesis may be blocked by use of aminopterin. Thus, unfused myeloma cells will not be supported by hypoxanthine, aminopterin, and thymidine (HAT) medium. Similarly, the unfused nonmalignant immunized spleen cells have only a finite number of generations and will not survive in HAT for more than a few days. The fused hybrid cells, on the other hand, will continue to reproduce because they possess the malignant quality of the myeloma parent and are able to survive in the selective medium by virtue of metabolic pathways deriving from the spleen cell parent.

The hybridomas may be cloned using the limited dilution method or the solid gel media method. The preferred cloning method is the limited dilution method. In this method, a hybridoma suspension is proportionately divided among a series of sterile wells. Visual appearance of colonies usually takes one to two weeks. The wells having the fewest hybridomas, showing single clones, are then evaluated for antibody production.

Once the hybridoma of choice has been selected and cloned, the desired monoclonal antibody may be produced in vitro or in vivo. The purest monoclonal antibody is produced in vitro by culturing the desired hybridoma in a suitable medium for a suitable length of time followed by recovering the desired antibody from the supernatant. The suitable medium and the suitable length of culturing time are known or are readily determined. This in vitro technique produces monoclonal antibody essentially free from other nonspecific antihuman immune globulins. However, this method may not produce a sufficient quantity of a sufficient concentration of monoclonal antibody for some purposes since the concentration of antibody obtained is relatively low.

Much higher concentrations (high titer) of slightly less pure monoclonal antibody may be produced using the in vivo method. In this method, the desired hybridoma is injected into mice, preferably syngenic or semisyngenic mice, causing formation of antibody-producing tumors after a suitable incubation time. These tumors will produce a relatively high concentration of the desired antibody in the bloodstream and peritoneal exudate (ascites) of the host mouse. Although these host mice also have normal antibodies in their blood and ascites, the concentration of these normal antibodies is low and these normal antibodies are not usually antihuman in their specificity.

The hybridomas of the present invention may also be used as a source of genetic material. For example, the hybridomas may be fused with other cells to provide still other novel hybridomas having the same secretory capabilities as SDW18.1.1 and providing antibodies having the same specificity. Such fusion of the subject hybridoma to other cells may result in the production of antibodies having different heavy polypeptide chains, providing other classes or subclasses of antibodies such as IgM, IgA, $IgG_2$, IgD, IgE, etc.

Although only a single novel hybridoma producing a single monoclonal antibody against cachectin/TNF antigen is described, Applicants intend the present invention to encompass all monoclonal antibodies which exhibit the characteristics described herein. The monoclonal antibody of the present invention to cachectin/TNF belongs to the subclass IgG1. The other classes and subclasses of IgG antibodies differ from one another in their "fixed" regions, i.e. areas having the same amino acid sequences. However, these antibodies will also have a "variable" region which is functionally identical, i.e. antigen specific, regardless of which antibody class or subclass to which the antibody belongs. Hence, a monoclonal antibody exhibiting the characteristics described herein may be of class IgM, IgA and so forth. Differences among these classes or subclasses will not affect the selectivity of the reaction pattern of the monoclonal antibody but may affect the reaction of the antibody with other materials. Although the antibody of the present invention belongs to class IgG1, Applicants intend that all antibodies having the patterns of reactivity illustrated herein are included within the present invention regardless of the immunoglobulin class or subclass to which they belong. Furthermore, for many applications, the entire monoclonal antibody molecule need not be used but only a fragment of the molecule having intact antigen-binding sites will suffice.

Although only a single hybridoma is described here, Applicants intend the present invention to encompass all methods for preparing the monoclonal antibodies described above employing the hybridoma technique described herein. One skilled in the art could follow the immunization, fusion, selection and cloning methods provided herein and obtain other hybridomas capable of producing monoclonal antibodies having the reactivity characteristics disclosed herein. Since the novel hybridoma produced from a known mouse myeloma cell line and spleen cells from a known species of mouse is best characterized by description of the antibody produced by the hybridoma, all hybridomas producing antibody having the reactivity characteristics described above are included within the subject invention, as are methods for making this antibody which employ the hybridoma.

It has now been found that cachectin is the principal mediator in both endotoxin-induced shock as well as tumor necrosis. [Nature, Vol. 320, No. 6063, pp. 584–588, 17 Apr. 1986]Applicants have successfully shown this to be true through passive immunization of baboons against endogenous cachectin. The baboons were subsequently infused with an $LD_{100}$ dose of live *Escherichia coli*. Control animals (not immunized against cachectin) developed hypotension followed by lethal renal and pulmonary failure. Neutralizing monoclonal anti-cachectin antibody fragments [F(ab')$_2$] administered to baboons only one hour before bacterial challenge, protected against shock but did not prevent critical organ failure. Complete protection against shock, vital organ dysfunction, persistent stress hormone release and death was conferred by administration of cachectin monoclonal antibodies 2 hours before bacterial infusion. These results indicate that cachectin is a mediator of fatal bacteremic shock, and suggest that cachectin antibodies offer a potential therapy for life-threatening infection. Thus, through passive immunization with cachectin antibodies, the deleterious effects of cachectin, such as septic shock, can be prevented or at least reduced. This invention thus contemplates a composition containing cachectin antibody for passive immunization of mammals against the effects of endotoxin. Additionally, this invention further contemplates an assay kit for the detection of human tumor necrosis factor, said kit comprising monoclonal antibody or antibody fragments reactant to cachectin, as well as other reagents and directions for use of such kit.

Accordingly, the present invention is also directed to in vivo and in vitro methods of diagnosis as well as therapy employing the monoclonal antibody to cachectin/TNF as well as anti-idiotype antibodies raised thereto. These techniques may be employed using the cachectin/TNF antibody or the anti-idiotype antibody alone, or in combination with other antibodies. For many applications, the antibodies will be labeled with a compound which imparts a detecting signal, providing cytotoxicity, providing for localizing electromagnetic radiation, or the like. Labels may include radionuclides, enzymes, fluorescent moieties, toxins or the cytotoxic fragment of toxins, particles, metals, metalloids, etc. The antibodies may be incorporated in liposome membranes or modified with lipids so as to be incorporated in such membranes. The antibodies by themselves or labeled may be used in in vitro diagnosis for measuring the presence of antigens associated with cachectin/TNF, for in vivo diagnosis for introduction into a host, e.g., intravenously, in a physiologically acceptable carrier, e.g., phosphate buffered saline, or may be introduced for therapeutic purposes in the same manner. Moreover, the antibodies of the present invention may be employed in methods and compositions for assaying cachectin/TNF, for diagnosing and treating disease states such as cachexia, septic shock, and related diseases and for the preparation of passive vaccines against these diseases. The amount of antibody employed will vary depending upon the particular application. The use of antibodies for diagnostic and therapeutic purposes has been extensively described in the literature.

Treatment of disease states such as cachexia may be accomplished by administration of a therapeutically effective amount of cachectin/TNF antibody to an individual in need of such treatment. By selective reaction with cachectin/TNF antigen, the effective amount of cachectin/TNF antibody will neutralize the excess of antigen, thus ameliorating the effects of the excess, such as undesirable weight loss. Diagnostic and therapeutic compositions comprising effective amounts of cachectin/TNF antibody in admixture with diagnostic or pharmaceutically acceptable carriers, respectively, are also included within the present invention.

In addition to the discovery of the above-described hydridoma cell line and the monoclonal antibodies produced therefrom, it has also been discovered that another set of polyclonal, polyspecific antibodies can be produced which are reactive with the monoclonal antibodies described herein. These polyclonal antibodies are, in effect, antibodies against antibodies and a subset is called anti-idiotype antibodies. By introducing anti-idiotype antibodies into the cachectin/TNF-TNF receptor reaction, a competitive reaction is set up between the anti-idiotype and the cachectin/TNF molecule which may result in less binding of the cachectin/TNF molecule with its cellular receptor. Thus, the anti-idiotype antibody can block the cachectin/TNF ligand complex from binding with its receptor, thereby possibly altering the deleterious effects of cachectin/TNF.

The present invention is further illustrated by the following examples which are not intended to limit the effective scope of the claims.

EXAMPLE

Recombinant human tumor necrosis factor (hTNF) (Genentech, Inc.) was emulsified in complete Freund's adjuvant. The equivalent of 17 micrograms of hTNF was injected subcutaneously into two mice (C57B1/6×Balb/c F1 female, Charles River Kingston). One month later, the spleens of these two mice were surgically exposed and 10 micrograms of hTNF in 100 microliters of phosphate-buffered saline ("PBS") were injected into each mouse intrasplenically. The spleens were placed back into the body cavities and the incisions were closed.

Three days later, the spleens were removed and carefully teased apart in Dulbecco's modified Eagle's medium (Grand Island Biological Company, Grand Island, N.Y.) with 4.5 grams per liter glucose and .10% fetal bovine serum to yield a single-cell suspension.

These immunized spleen cells were fused with the P3-× 63-Ag8.653 myeloma cell line (American Type Culture Collection) utilizing the protocol described in *Monoclonal Antibodies*, R. Kennett, K. Bechtol and T. McKearn (Eds.), plenum press (1980). The fused cells were plated onto macrophage feeder layers using the protocol described by Fazekas de St. Groth and Scheidegger, J. *Immunol. Methods*, 35,1–21 (1980), and allowed to grow until macroscopic colonies were observed.

Colonies were tested for the production of antibody against hTNF using an immunoblotting assay. Nitrocellulose sheets were immersed in PBS and blotted dry. A quantity of 5 microliters of hTNF (initially obtained from Genentech, Inc., and later obtained from Chiron Corp.) at a concentration of 0.1 microgram per milliliter were dotted onto spots on the nitrocellulose plate through wells in a Bio-Rad dot-blotting apparatus. The nitrocellulose was blocked using a solution of 1% bovine serum albumin in PBS. A quantity of 100 microliters of the supernatant above the cultured hybridoma colonies was added to each dot-blot and well, and incubated for 45 minutes. The clones which reacted positively were visualized by the subsequent use of a VECTASTAIN (trademark) avidin-biotin-peroxidase system (Vector, Inc.) according to the instructions of the manufacturer.

Initially, thirteen positive clones were identified. Four clones appeared to show false positives because they also showed positive in the absence of antigen. One clone (#23) showed positive with antigen material obtained from Genentech, Inc. but not with antigen material obtained from Chiron Corp. Four clones (#27, #37, #42 and #156) appeared to lose activity during further propagation. These four clones and three other clones (#299, #433 and #471) were set aside for further characterization.

One clone (#18) exhibited consistent reactivity and retained this reactivity during subcloning. Subcloning was achieved by limited dilution on macrophage feeder layers. Dilute suspensions of a given clone were plated onto 96-well plates such that less than a third of the wells were positive for growth.

Each subcloning was designated by a period. Hence, the designation —18.1.1—means that clone #18 was subcloned twice and the first well which showed growth was chosen for further subcloning each time. The subject hybrid antibody was demonstrated by standard techniques to be of class IgG1.

This invention may be embodied in other forms or carried out in other ways without departing from the spirit or essential characteristics thereof. The present disclosure is therefore to be considered as in all respects illustrative and not restrictive, the scope of the invention being indicated by the appended Claims, and all changes which come within the meaning and range of equivalency are intended to be embraced therein.

What is claimed is:

1. A method of ameliorating or preventing septic shock which comprises administering to a mammalian patient suspected of having a need for such administration an effective amount of a monoclonal antibody exhibiting the characteristics of a monoclonal antibody as produced by hybridoma cell line having the identifying characteristics of A.T.C.C. Accession No. HB 9228.

2. The method of mitigating claim 1 wherein the monoclonal antibody is produced from a hybridoma cell line having the identifying characteristics of A.T.C.C. Accession No. HB 9228.

* * * * *